United States Patent
Anand et al.

(10) Patent No.: US 6,914,064 B2
(45) Date of Patent: Jul. 5, 2005

(54) 1,4-DISUBSTITUTED PIPERAZINE DERIVATIVES USEFUL AS URO-SELECTIVE $\alpha_1$-ADRENOCEPTOR BLOCKERS

(75) Inventors: Nitya Anand, Uttar Pradesh (IN); Sanjay Jain, Pune (IN); Neelima Sinha, Uttar Pradesh (IN); Anita Chugh, New Delhi (IN); Laxminarayan G. Hegde, New Delhi (IN); Jang Bahadur Gupta, Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/998,115

(22) Filed: Nov. 30, 2001

(65) Prior Publication Data

US 2002/0156085 A1 Oct. 24, 2002

(30) Foreign Application Priority Data

Nov. 30, 2000 (IN) .............................. 1097/00

(51) Int. Cl.$^7$ ..................... A61K 31/496; C07D 403/06
(52) U.S. Cl. .................................. 514/254.08; 544/373
(58) Field of Search ...................... 544/373; 514/254.08

(56) References Cited

U.S. PATENT DOCUMENTS

| | | | |
|---|---|---|---|
| 4,479,954 A | 10/1984 | Hirose et al. | 424/251 |
| 4,524,206 A | 6/1985 | New et al. | 544/230 |
| 4,598,078 A | 7/1986 | Ishizumi et al. | 514/252 |
| 6,083,950 A | 7/2000 | Anand et al. | 514/252 |
| 6,090,809 A | 7/2000 | Anand et al. | 514/252 |

FOREIGN PATENT DOCUMENTS

| | | |
|---|---|---|
| AT | 387 773 B | 3/1989 |
| EP | 0 109 562 A1 | 5/1984 |
| EP | 0 111 226 A1 | 6/1984 |
| EP | 0 711 757 A1 | 5/1996 |
| EP | 0748800 A2 * | 12/1996 |
| JP | 59036661 | 2/1984 |
| JP | 60-204784 | 10/1985 |
| JP | 02-235865 | 9/1990 |
| WO | WO 98/37893 | 9/1998 |
| WO | WO 98/51298 | 11/1998 |

OTHER PUBLICATIONS

Hieble et al., "Recent advances in the identification of alpha1– and alpha2–adrenoceptor subtypes: therapeutic implications", *Expert Opinion on Investigational Drugs 6*, pp. 367–387 (1997).

Kenny et al., "Pharmacological Options in the Treatment of Benign Prostatic Hyperplasia", *J. Med. Chem. 40*, pp. 1293–1315 (1997).

Cross, et al., "Substituted trifluoromethyl phenyl piperazines as anoretic–agents", *Eur. J. Med. Chem.—Chimica Therapeutica 12*, pp 173–176 (1977).

Van Steen, et al., "A Series of N4–Imidoethyl Derivatives of 1–(2,3–Dihydro–1,4–benzodioxin–5–yl)piperazine as 5–HT$_{1A}$ Receptor Ligands: Synthesis and Structure–Affinity Relationships", *J. Med. Chem. 38*, pp. 4303–4308 (1995).

Ishizumi, et al., "Synthesis and Anxiolytic Activity of N–Substituted Cyclic Imides (1R*,2S*, 3R*, 4S*)–N–[4–[4–(2–Pyrimidinyl)–1–piperazinyl]buty]–2,3–bicyclo [2.2.1]heptanedicarboximide (Tandospirone) and Related Compounds$^{1,2}$)", *Chem. Pharm. Bull. 39 (9)*, pp. 2288–2300 (1991).

New, et al., "Buspirone Analogues. 2. Structure–Activity Relationships of Aromatic Imide Derivatives", *J. Med. Chem, 29*, pp. 1476–1482 (1986).

Korgaonkar, et al., "Synthesis of N–[3–(4–Aryl–1– piperazinyl)propyl]–4, 4–bis(4–methoxyphenyl)piperidine,–2, 6–diones/Tetrahydrophthalimides/Camphorimides as Sedatives", *J. Indian Chem. Soc. vol. LX*, pp. 874–876 (1983).

Khadilkar & Samant, "Synthesis and Pharmacology of Some 2–[3–(4–Aryl–1–piperazinyl)propyl]–1H–benz[de] isoquinolin–1,3(2H)–diones/2,5–pyrrolinediones", *J. Indian Chem. Soc.: vol. LXIII*, pp. 529–530 (1986).

Samant & Kulkarni, "N–(N$^4$–Aryl–N$^1$ piperazinylmethyl)– 4–(4–methoxyphenyl)–piperdine–2,6–diones: CNS Depressants", *J. Indian Chem. Soc. vol. LV*, pp. 819–821 (1978).

Samant & Kulkarni, "Synthesis and Pharmacology of N–(N$^4$–Aryl–N$^1$–Piperazinylalkyl) Phthalimides: CNS Depressants", *J. Indian Chem. Soc. vol. LVI*, pp. 1002–1005 (1979).

Michel, et al., "Identification of a single $\alpha_1$–adrenoceptor corresponding to the $\alpha_{1A}$–subtype in rat submaxillary gland", *Br. J. Pharmacol. 98*, pp 883–889 (1989).

U'Prichard, et al., "Prazosin: Differential Affinities for Two Populations of $\alpha$–Noradrenergic Receptor Binding Sites", *Eur. J. of Pharm. 50*, pp. 87–89 (1978).

(Continued)

Primary Examiner—Emily Bernhardt
(74) Attorney, Agent, or Firm—Jayadeep R. Deshmukh, Esq.; George E. Heibel, Esq.

(57) ABSTRACT

The present invention relates to a novel 1,4-disubstituted piperazine derivatives of Formula I,

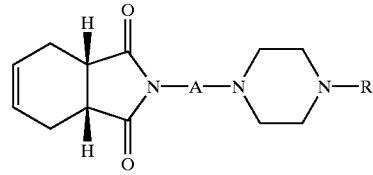

FORMULA-I and their pharmaceutically acceptable acid addition salts having excellent uro-selective $\alpha_1$-adrenoceptor antagonistic activity exceeding those of previously described compounds. The compounds of the present invention hold promise for treating the symptoms of benign prostatic hyperplasia (BPH). The invention also relates to methods for making the novel compounds, pharmaceutical compositions containing the compounds, and method of treating the symptoms of benign prostatic hyperplasia using the compounds.

7 Claims, No Drawings

OTHER PUBLICATIONS

Brune, et al., "Effects of Selective and Nonselective Alpha–1–Adrenoceptor Antagonists on Intraurethral and Arterial Pressures in Intact Conscious Dogs", *Pharmacology* 53, pp. 356–368 (1996).

Zagidullin, "N–(.beta.–Aminoethyl)piperazine and its derivatives in aminomethylation reactions", *Zh. Obshch. Khim.*, vol. 16, No. 1, pp. 247–253 (1991).

* cited by examiner

1,4-DISUBSTITUTED PIPERAZINE DERIVATIVES USEFUL AS URO-SELECTIVE $\alpha_1$-ADRENOCEPTOR BLOCKERS

FIELD OF THE INVENTION

The present invention relates to certain novel 1,4-disubstituted piperazine derivatives of Formula I,

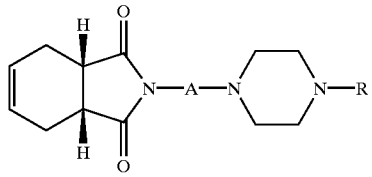

FORMULA-I and their pharmaceutically acceptable acid addition salts having excellent uro-selective $\alpha_1$-adrenoceptor antagonistic activity exceeding those of previously described compounds. The compounds of the present invention hold promise for treating the symptoms of benign prostatic hyperplasia (BPH). The invention also relates to methods for making the novel compounds, pharmaceutical compositions containing the compounds, and method of treating the symptoms of benign prostatic hyperplasia using the compounds.

BACKGROUND OF THE INVENTION

Benign prostatic hyperplasia (BPH) is a common disease in aging males and a substantial percentage of men with BPH develop a bladder obstruction. The obstruction caused by BPH is thought to be attributable to two main components i.e. a static component related to enlarged prostatic tissue mass and a dynamic component involving excessive contraction of prostate and urethra. The most successful therapies are based on α-adrenergic receptor antagonism and androgen levels modulation by 5α-reductase inhibitors. 5α-reductase inhibitors are of limited effectiveness in terms of immediate symptomatic and urodynamic relief. $\alpha_1$-adrenergic receptors antagonists appear to be much more effective and provide immediate subjective symptomatic improvements and are, therefore, the preferred modalities of treatment in the control of symptoms of benign prostatic hyperplasia. $\alpha_1$-Adrenoceptors are also present in blood vessels and play an important role in the regulation of blood pressure. Thus $\alpha_1$-adrenoceptor antagonists are of particular importance as they were originally developed as antihypertensive agents and are likely also to have a beneficial effect on lipid dysfunction and insulin resistance, which are commonly associated with essential hypertensions.

The drugs most often used for BPH are the long acting $\alpha_1$-adrenoceptor antagonists, terazosin, doxazosin and tamsulosin, as shown below:

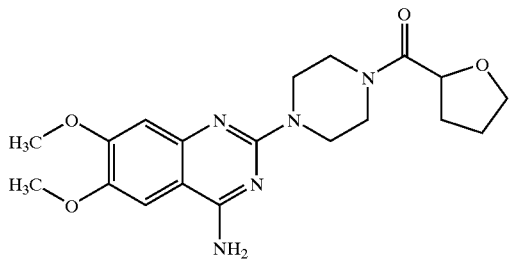

TERAZOSIN

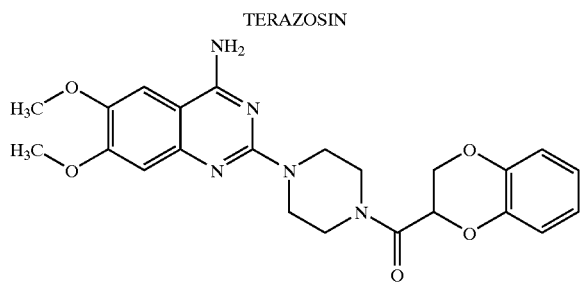

DOXAZOSIN

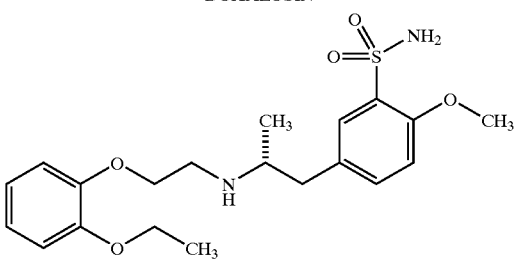

(R)-(-)-TAMSULOSIN

However, these drugs are associated with vascular side effects (e.g. postural hypertension, syncope, dizziness, headache etc.) due to lack of selectivity of action between prostatic and vascular $\alpha_1$-adrenoceptors.

Over the past decade, there has been an intensive search for "uroselective" $\alpha_1$-adrenoceptor antagonists for BPH, which would avoid the cardiovascular side effects, associated with currently used drugs. Clearly, $\alpha_1$-adrenoceptor antagonists which have inherently greater selectivity for prostatic $\alpha_1$-adrenoceptors offer the potential of increased urodynamic benefits. This underscores the importance of the discovery of antagonists which will confer urodynamic improvement without the side effects associated with existing drugs.

Recently, three subtypes of $\alpha_1$-receptors namely $\alpha_{1A}$, $\alpha_{1B}$; and $\alpha_{1D}$ have been identified which can provide a key development to improve the pharmacological selectivity of $\alpha_1$ blockers. These subtypes have different tissue distribution with the $\alpha_{1A}$ receptors predominating lower urinary tract tissue and less prevalent in the vasculature. This makes it possible to develop agents with selective action against pathological urodynamic states. A uroselective $\alpha_{1A}$-antagonist could have greater efficacy if dose escalation is not limited to cardiovascular side effects and a more complete blockade of prostatic $\alpha_1$-adrenoceptors could be attained. Compounds have been evaluated for potency against agonist or stimulation-induced increase in urethral pressure relative to blood pressure reduction or blockade of agonist-induced blood pressure. Many selective antagonists have been described by Hieble et al in *Exp opin Invest Drugs*; 6, 367–387 (1997) and by Kenny et. al. in *J. Med.*

Chem.; 40, 1293–1315 (1997). Structure activity relationships in many of these structural series have been studied in details and numerous highly selective compounds have been identified.

The present invention is directed to the development of novel $\alpha_1$-antagonists, namely, 1,4-disubstituted piperazine compounds, with greater selectivity of action against a $\alpha_{1A}$-adrenoceptors and which would thus offer relief from the symptoms of BPH.

There are many description in the literature about the pharmacological activities associated with phenyl piperazines, *Eur. J. Med. Chem.*—Chimica Therapeutica, 12, 173–176 (1977), describes substituted trifluoromethyl phenyl piperazines having cyclo-imido alkyl side chains shown below.

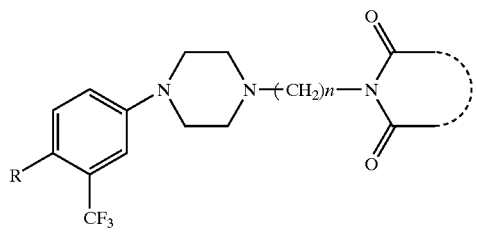

These compounds are potential anorectic agents with no CNS side effects. Other related compounds which have been prepared as anxiolytic, neuroleptic, anti-diabetic and anti-allergic agents are described in the following references:

Yukihiro et al; PCT Appl. WO 98/37893 (1998).
Steen et al; *J. Med. Chem.*, 38, 4303–4308 (1995).
Ishizumi et al. *Chem. Pharm. Bull*; 39 (9), 2288–2300 (1991).
Kitaro et al; JP 02-235865 (1990).
Ishizumi et al; U.S. Pat. No. 4,598,078 (1986).
New et. al; J. Med. Chem, 29, 1476–1482 (1986).
Shigeru et al, JP 60-204784 (1985).
New et al, U.S. Pat. No. 4,524,206 (1985).
Korgaonkar et al; *J. Indian Chem. Soc.*, 60, 874–876 (1983)

The synthesis and pharmacology of some 2-[3-(4-aryl-1-piperazinyl) propyl]-1H-benz(de) isoquinolin-1,3-(2H)-diones/2,5-pyrrolidinediones (*J. Indian. Chem. Soc.*, Vol., LXIII, 529–530 (1986), of N-(N⁴-aryl-N¹-piperozinylmethyl)-4-(4-methoxyphenyl)piperidine-2,6-diones [J. Indian Chem. Soc., Vol. LV, 819–821 (1978)], and of N- (N⁴-arylpiperazinylalkyl)-phthalimides (*J. Indian. Chem. Soc.*, Vol. LVI, 1002–1005 (1979)] have been reported. The compounds were shown to exhibit antihypertensive and CNS depressant activity in experimental animals.

However, none of the above mentioned references disclose or suggest the selective $\alpha_1$-adrenoceptor blocking activity of the compounds disclosed therein and thus their usefulness in the treatment of symptoms of benign prostate hyperplasia did not arise.

The synthesis of 1-(4-arylpiperazin-1-yl)-ω-[N-(α, ω-dicarboximido)]-alkanes useful as uro-selective $\alpha_1$-adrenoceptor blockers are disclosed in U.S. Pat. Nos. 6,083,950 and 6,090,809. These compounds had good a $\alpha_1$-adrenergic blocking activity and selectivity and one of the compounds is in phase II clinical trials.

It has now been discovered that structural modification of these compounds from glutarimide to tetrahydrophthalimide enhances the adrenoceptor blocking acitvity and also greatly increases the selectivity for $\alpha_{1A}$ in comparison to $\alpha_{1B}$-adrenoceptor blocking activity, an essential requirement for compounds to be good candidates for treatment of BPH.

OBJECTS OF THE INVENTION

An object of the present invention is to provide novel arylpiperazine derivatives that exhibit greater $\alpha_{1A}$-adrengeric blocking potency and more selectivity than available known compounds and are useful for treatment of benign prostatic hyperplasia.

It is also an object of the invention to provide a method for synthesis of the novel compounds.

It is a further object of the present invention to provide compositions containing the novel compounds which are useful in the treatment of benign prostatic hyperplasia.

SUMMARY OF THE INVENTION

The above-mentioned objectives are achieved by a novel class of piperazine derivatives of general Formula I, as shown below,

FORMULA-I

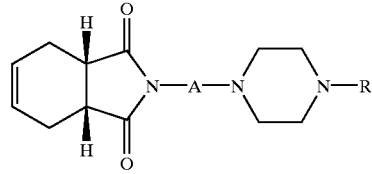

its pharmaceutically acceptable salts, amides, enantiomers, diastereomers, N-oxides, prodrugs, metabolites or their polymorphs, wherein A is a straight or branched $C_1$–$C_4$ alkyl chain; R is cinnamyl, benzyl, substituted benzyl, phenyl, mono- or disubstituted phenyl group substituted with the substituents independently selected from the group consisting of halogen, hydroxy, $C_1$–$C_6$ alkyl, $C_1$–$C_6$ alkoxy, trifluoromethyl, nitro and trifluoroalkoxy group, or (dihalodiphenyl) methyl.

Halogen of Formula I may be selected from the group consisting of chloro, fluoro, iodo; $C_1$–$C_6$ alkyl may be selected from methyl, ethyl, n-propyl, isopropyl, butyl, tert-butyl; and $C_1$–$C_6$ alkoxy may be selected from methoxy, ethoxy, n-propoxy, isopropoxy, or hexyloxy.

The present invention also provides pharmaceutical compositions for the treatment of benign prostatic hyperplasia. These compositions comprise an effective amount of at least one of the compounds of Formula I, or an effective amount of at least one physiologically acceptable acid addition salt thereof, with a pharmaceutically acceptable carrier.

An illustrative list of particular compounds of the invention is given below:

| Compound No. | Name |
|---|---|
| 1. | 2-[3-{4-(2-Methoxyphenyl)piperazin-1-yl}propyl]-3a,4,7,7a-tetrahydro-1H-isoindole-1,3(2H)-dione; |
| 2. | 2-[3-{4-(3-Chlorophenyl)piperazin-1-yl}propyl]-3a,4,7,7a-tetrahydro-1H-isoindole-1,3(2H)-dione; |
| 3. | 2-[3-{4-(2-Methylphenyl)piperazin-1-yl}propyl]-3a,4,7,7a-tetrahydro-1H-isoindole-1,3(2H)-dione; |
| 4. | 2-[3-{4-(4-Fluorophenyl)piperazin-1-yl}propyl]-3a,4,7,7a-tetrahydro-1H-isoindole-1,3(2H)-dione; |
| 5. | 2-[3-{4-(3-Trifluoromethylphenyl)piperazin-1-yl}propyl]-3a,4,7,7a-tetrahydro-1H-isoindole-1,3(2H)-dione; |
| 6. | 2-[3-{4-(2-Fluorophenyl)piperazin-1-yl}propyl]-3a,4,7,7a-tetrahydro-1H-isoindole-1,3(2H)-dione; |
| 7. | 2-[3-{4-(3,4-Dimethylphenyl)piperazin-1-yl}propyl]-3a,4,7,7a-tetrahydro-1H-isoindole-1,3(2H)-dione; |
| 8. | 2-[3-{4-(2-Methoxy-5-fluorophenyl)piperazin-1-yl}propyl]-3a,4,7,7a-tetrahydro-1H-isoindole-1,3(2H)-dione; |
| 9. | 2-[3-{4-(2-Ethylphenyl)piperazin-1-yl}propyl]-3a,4,7,7a-tetrahydro-1H-isoindole-1,3(2H)-dione; |
| 10. | 2-[3-{4-(2,4-Difluorophenyl)piperazin-1-yl}propyl]-3a,4,7,7a-tetrahydro-1H-isoindoie-1,3(2H)-dione; |
| 11. | 2-[3-{4-(2-Ethoxyphenyl)piperazin-1-yl}propyl]-3a,4,7,7a-tetrahydro-1H-isoindole-1,3(2H)-dione; |
| 12. | 2-[3-{4-(2-Methyl-5-chlorophenyl)piperazin-1-yl}propyl]-3a,4,7,7a-tetrahydro-1H-isoindole-1,3(2H)-dione; |
| 13. | 2-[3-{4-(Phenyl)piperazin-1-yl}propyl]-3a,4,7,7a-tetrahydro-1H-isoindole-1,3(2H)-dione; |
| 14. | 2-[3-{4-(Benzyl)piperazin-1-yl}propyl]-3a,4,7,7a-tetrahydro-1H-isoindole-1,3(2H)-dione; |
| 15. | 2-[3-{4-(Cinnamyl)piperazin-1-yl}propyl]-3a,4,7,7a-tetrahydro-1H-isoindole-1,3(2H)-dione; |
| 16. | 2-[3-{4-(4-Nitrophenyl)piperazin-1-yl}propyl]-3a,4,7,7a-tetrahydro-1H-isoindole-1,3(2H)-dione; |
| 17. | 2-[3-{4-(3-Chloro-4-methylphenyl)piperazin-1-yl}propyl]-3a,4,7,7a-tetrahydro-1H-isoindole-1,3(2H)-dione; |
| 18. | 2-[3-{4-(4-Fluoro-2-methoxyphenyl)piperazin-1-yl}propyl]-3a,4,7,7a-tetrahydro-1H-isoindole-1,3(2H)-dione; |
| 19. | 2-[3-{4-(Bis-4-fluorophenyf)methylpiperazin-1-yl}propyl]-3a,4,7,7a-tetrahydro-1H-isoindole-1,3(2H)-dione; |
| 20. | 2-[3-{4-(2,4-Dichlorophenyl)piperazin-1-yl}propyl]-3a,4,7,7a-tetrahydro-1H-isoindole-1,3(2H)-dione; |
| 21. | 2-[3-{4-(2,4-Dimethoxyphenyl)piperazin-1-yl}propyl]-3a,4,7,7a-tetrahydro-1H-isoindole-1,3(2H)-dione; |
| 22. | 2-[3-{4-(2,6-Dimethylphenyl)piperazin-1-yl}propyl]-3a,4,7,7a-tetrahydro-1H-isoindole-1,3(2H)-dione; |
| 23. | 2-[3-{4-(2-Isopropoxyphenyl)piperazin-1-yl}propyl]-3a,4,7,7a-tetrahydro-1H-isoindole-1,3(2H)-dione; |
| 24. | 2-[3-{4-(2-Propoxyphenyl)piperazin-1-yl}propyl]-3a,4,7,7a-tetrahydro-1H-isoindole-1,3(2H)-dione; |
| 25. | 2-[3-{4-(2-n-Hexyloxyphenyl)piperazin-1-yl}propyl]-3a,4,7,7a-tetrahydro-1H-isoindole-1,3(2H)-dione; |
| 26. | 2-[3-{4-(2,5-Dimethoxyphenyl)piperazin-1-yl}propyl]-3a,4,7,7a-tetrahydro-1H-isoindole-1,3(2H)-dione; |
| 27. | 2-[3-{4-(4-tert-Butylphenyl)piperazin-1-yl}propyl]-3a,4,7,7a-tetrahydro-1H-isoindole-1,3(2H)-dione; |
| 28. | 2-[3-{4-(2-Methoxy-8-hydroxyphenyl)piperazin-1-yl}propyl]-3a,4,7,7a-tetrahydro-1H-isoindole-1,3(2H)-dione; |
| 29. | 2-[3-{4-(2-Methoxyphenyl)piperazin-1-yl}-3-methylpropyl]-3a,4,7,7a-tetrahydro-1H-isoindole-1,3(2H)-dione; |
| 30. | 2-[3-{4-(2-Methoxyphenyl)piperazin-1-yl}-2-methylpropyl]-3a,4,7,7a-tetrahydro-1H-isoindole-1,3(2H)-dione; |
| 31. | 2-[3-{4-(2-Ethoxyphenyl)piperazin-1-yl}-3-methylpropyl]-3a,4,7,7a-tetrahydro-1H-isoindole-1,3(2H)-dione; |

DETAILED DESCRIPTION OF THE INVENTION

The compounds of the present invention may be prepared by one of the reaction sequences (Schemes I and II) shown below to yield compounds of Formula I wherein A is a straight or branched $C_1$–$C_4$ alkyl chain; R is cinnamyl, benzyl, substituted benzyl, phenyl, mono- or disubstituted phenyl group substituted with the substituents independently selected from the group consisting of halogen, hydroxy, $C_1$–$C_6$ alkyl, $C_1$–$C_6$ alkoxy, trifluoromethyl, nitro and trifluoroalkoxy group, or (dihalodiphenyl) methyl.

Scheme I

The compounds of the Formula I can be prepared by condensation of piperazine derivatives of Formula III with the anhydride of Formula II, wherein A and R are the same as defined above, preferably in a solvent selected from the group consisting of pyridine, n-butanol, benzene and xylene while refluxing.

SCHEME-I

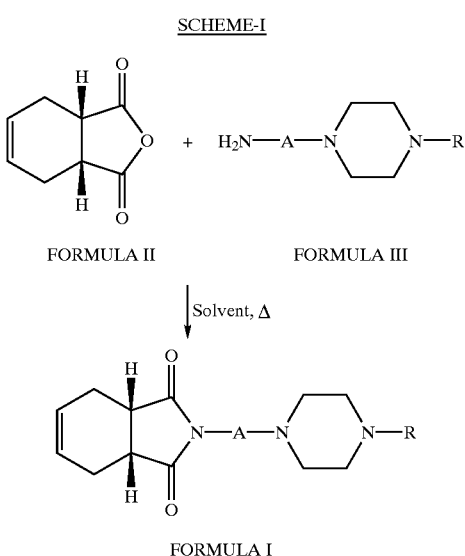

FORMULA II     FORMULA III

↓ Solvent, Δ

FORMULA I

Scheme II

The compounds of the Formula I, wherein A and R are the same as defined above, can also be synthesized following the reaction sequence as shown in Scheme II, by condensation of 1-(ω-haloalkyl)-cis-3a,4,7,7a-tetrahydrophthalimide of Formula IV, wherein A is the same as defined above, with 1-substituted piperazine of the Formula V, wherein R is the same as defined before.

SCHEME-II

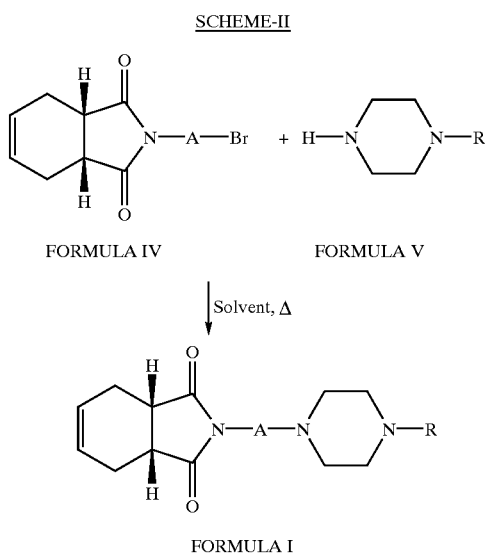

FORMULA IV     FORMULA V

↓ Solvent, Δ

FORMULA I

Pharmaceutically acceptable, non toxic, acid addition salts of the compounds prepared according to the present invention having the utility of the free bases of Formula I may be formed with inorganic or organic acids, by methods well known in the art and may be used in place of the free bases. Representative examples of suitable acids for formation of such acid addition salts are malic, fumaric, benzoic, ascorbic, pamoic, succinic, bismethylene, salicylic, methanesulphonic ethanedisulphonic, acetic, propionic, tartaric, citric, gluconic, aspartic, stearic, palmitic, itaconic, glycolic, p-aminobenzoic, glutamic, benzenesulfamic, phosphoric, hydrobromic, sulfuric, hydrochloric, and nitric acids, and the like.

The present invention also includes within its scope prodrugs of the compounds of Formula I. In general, such prodrugs will be functional derivatives of these compounds which are readily converted in vivo into the defined compounds. Conventional procedures for the selection and preparation of suitable prodrugs are known.

The invention also includes the enantiomers, diastereomers, N-oxides, pharmaceutically acceptable salts, amides and polymorphic forms of these compounds, as well as metabolites having the same activity. The invention further includes pharmaceutical compositions comprising the molecules of Formula I, or prodrugs, metabolites, enantiomers, diastereomers, N-oxides, pharmaceutically acceptable salts or polymorphic forms thereof, in combination with a pharmaceutically acceptable carrier and optionally included excipients.

In yet another aspect, the invention is directed to methods for selectively blocking $\alpha_{1A}$ receptors by delivering in the environment of said receptors, e.g. to the extracellular medium (or by administering to a mammal possessing said receptors) an effective amount of the compounds of the invention.

While the invention has been described by reference to specific embodiments, this was for purposes of illustration only. Numerous alternative embodiments will be apparent to those skilled in the art and are deemed to be within the scope of the invention.

The examples mentioned below demonstrate the general synthetic as well as the specific preparation for the preferred compound. The examples are given to illustrate the details of the invention and should not be constrained to limit the scope of the present invention.

EXAMPLE

Preparation of 2-[3-{4-(2-methoxyphenyl) piperazine-1-yl}propyl]-3a,4,7,7a-tetrahydro-1H-isoindole-1,3(2H)-dione Scheme I A mixture of 1-amino-3-[4-(2-methoxyphenyl) piperazine-1-yl]propane (0.498 g, 2.0 mmol) and cis-1,2,3,6-tetrahydrophthalic anhydride (0.273 g, 1.8 mmol) was refluxed in pyridine (10 ml) for about 5 hrs. After the reaction was over, solvent was removed under vacuum and the residue was dissolved in chloroform (25 ml). The chloroform phase was washed with water (2×15 ml), dried over anhydrous sodium sulphate and concentrated under vacuum. The crude compound so obtained was purified by column chromatography over silica gel (100–200 mesh) using chloroform as an eluent (yield=0.502 g, 72%).

The hydrochloride salt was prepared by the addition of molar quantity of ethereal hydrogen chloride solution to the etheral solution of free base and collected the precipitated solid by filtration (m.p. 184–185° C.).

Scheme II

A mixture of 1-(3-bromopropyl)-cis-3a, 4,7,7a-tetrahydrophthalimide (7.04 g, 25.88 mmol), 1-(2-methoxyphenyl)piperazine hydrochloride (5.32 g, 23.29 mmol), potassium carbonate (7.14 g, 51.76 mmol) and potassium iodide (0.026 g, 1.55 mmol) in N,N-dimethylformamide (27 ml) was heated at 75–80° C. for about 12 hours. After the reaction was over, solvent was evaporated under vacuum, residue was suspended in water (130 ml) and extracted the compound with dichloromethane (2×65 ml). The combined dichloromethane layer was washed with water (2×30 ml), dried over anhydrous sodium sulphate and concentrated the solvent under vacuum to yield 8.308 g (93%) of the crude base. The compound so obtained was converted into its hydrochloride salt (m. pt. 184–185° C.).

An illustrative list of the compounds of the invention which were synthesised by one or more of the above described methods is now given.

| Compound No. | Name |
|---|---|
| 1. | 2-[3-{4-(2-Methoxyphenyl)piperazin-1-yl}propyl]-3a,4,7,7a-tetrahydro-1H-isoindole-1,3(2H)-dione hydrochloride; m.p. 184–185° C. |
| 2. | 2-[3-{4-(3-Chlorophenyl)piperazin-1-yl}propyl]-3a,4,7,7a-tetrahydro-1H-isoindole-1,3(2H)-dione hydrochloride; m.p. 221–223° C. |
| 3. | 2-[3-{4-(2-Methylphenyl)piperazin-1-yl}propyl]-3a,4,7,7a-tetrahydro-1H-isoindole-1,3(2H)-dione hydrochlolide; m.p. 186–187° C. |
| 4. | 2-[3-{4-(4-Fluorophenyl)piperazin-1-yl}propyl]-3a,4,7,7a-tetrahydro-1H-isoindole-1,3(2H)-dione hydrochloride; m.p. 228–230° C. |
| 5. | 2-[3-{4-(3-Trifluoromethylphenyl)piperazin-1-yl}propyl]-3a,4,7,7a-tetrahydro-1H-isoindole-1,3(2H)-dione hydrochloride; m.p. 215–217° C. |
| 6. | 2-[3-{4-(2-Fluorophenyl)piperazin-1-yl}propyl]-3a,4,7,7a-tetrahydro-1H-isoindole-1,3(2H)-dione hydrochloride; m.p. 203–204° C. |
| 7. | 2-[3-{4-(3,4-Dimethylphenyl)piperazin-1-yl}propyl]-3a,4,7,7a-tetrahydro-1H-isoindole-1,3(2H)-dione hydrochloride; m.p. 194–196° C. |
| 8. | 2-[3-{4-(2-Methoxy-5-fluorophenyl)piperazin-1-yl}propyl]-3a,4,7,7a-tetrahydro-1H-isoindole-1,3(2H)-dione hydrochloride; m.p. 163–165° C. |
| 9. | 2-[3-{4-(2-Ethylphenyl)piperazin-1-yl}propyl]-3a,4,7,7a-tetrahydro-1H-isoindole-1,3(2H)-dione hydrochloride; m.p. 232.5–233.5° C. |
| 10. | 2-[3-{4-(2,4-Difluorophenyl)piperazin-1-yl}propyl]-3a,4,7,7a-tetrahydro-1H-isoindole-1,3(2H)-dione hydrochloride; m.p. 218.2–219° C. |
| 11. | 2-[3-{4-(2-Ethoxyphenyl)piperazin-1-yl}propyl]-3a,4,7,7a-tetrahydro-1H-isoindole-1,3(2H)-dione hydrochloride; m.p. 221.9–222.7° C. |
| 12. | 2-[3-{4-(2-Methyl-5-chlorophenyl)piperazin-1-yl}propyl]-3a,4,7,7a-tetrahydro-1H-isoindole-1,3(2H)-dione hydrochloride; m.p. 231–232° C. |
| 13. | 2-[3-{4-(Phenyl)piperazin-1-yl}propyl]-3a,4,7,7a-tetrahydro-1H-isoindole-1,3(2H)-dione hydrochloride; m.p. 231–232° C. |
| 14. | 2-[3-{4-(Benzyl)piperazin-1-yl}propyl]-3a,4,7,7a-tetrahydro-1H-isoindole-1,3(2H)-dione hydrochloride; m.p. 275–278° C. |
| 15. | 2-[3-{4-(Cinnamyl)piperazin-1-yl}propyl]-3a,4,7,7a-tetrahydro-1H-isoindole-1,3(2H)-dione hydrochloride; m.p. 263–265° C. |
| 16. | 2-[3-{4-(4-Nitrophenyl)piperazin-1-yl}propyl]-3a,4,7,7a-tetrahydro-1H-isoindole-1,3(2H)-dione hydrochloride; m.p. 259.5–261° C. |
| 17. | 2-[3-{4-(3-Chloro-4-methylphenyl)piperazin-1-yl}propyl]-3a,4,7,7a-tetrahydro-1H-isoindole-1,3(2H)-dione hydrochloride; m.p. 248–249° C. |
| 18. | 2-[3-{4-(4-Fluoro-2-methoxyphenyl)piperazin-1-yl}propyl]-3a,4,7,7a-tetrahydro-1H-isoindole-1,3(2H)-dione hydrochloride; m.p. 232–233° C. |
| 19. | 2-[3-{4-(Bis-4-fluorophenyl)methylpiperazin-1-yl}propyl]-3a,4,7,7a-tetrahydro-1H-isoindole-1,3(2H)-dione hydrochloride; m.p. 235–236° C. |
| 20. | 2-[3-{4-(2,4-Dichlorophenyl)piperazin-1-yl}propyl]-3a,4,7,7a-tetrahydro-1H-isoindole-1,3(2H)-dione hydrochloride; m.p. 210–211° C. |
| 21. | 2-[3-{4-(2,4-Dimethoxyphenyl)piperazin-1-yl}propyl]-3a,4,7,7a-tetrahydro-1H-isoindole-1,3(2H)-dione hydrochloride; m.p. 226–227° C. |
| 22. | 2-[3-{4-(2,6-Dimethylphenyl)piperazin-1-yl}propyl]-3a,4,7,7a-tetrahydro-1H-isoindole-1,3(2H)-dione hydrochloride; m.p. 223–224° C. |
| 23. | 2-[3-{4-(2-Isopropoxyphenyl)piperazin-1-yl}propyl]-3a,4,7,7a-tetrahydro-1H-isoindole-1,3(2H)-dione hydrochloride; m.p. 223–224° C. |
| 24. | 2-[3-{4-(2-Propoxyphenyl)piperazin-1-yl}propyl]-3a,4,7,7a-tetrahydro-1H-isoindole-1,3(2H)-dione hydrochloride; m.p. 193–194° C. |
| 25. | 2-[3-{4-(2-n-Hexyloxyphenyl)piperazin-1-yl}propyl]-3a,4,7,7a-tetrahydro-1H-isoindole-1,3(2H)-dione hydrochloride; m.p. 165–166° C. |
| 26. | 2-[3-{4-(2,5-Dimethoxyphenyl)piperazin-1-yl}propyl]-3a,4,7,7a-tetrahydro-1H-isoindole-1,3(2H)-dione hydrochloride; m.p. 193–195° C. |
| 27. | 2-[3-{4-(4-tert-Butylphenyl)piperazin-1-yl}propyl]-3a,4,7,7a-tetrahydro-1H-isoindole-1,3(2H)-dione hydrochloride; m.p. 264–265° C. |
| 28. | 2-[3-{4-(2-Methoxy-6-hydroxyphenyl)piperazin-1-yl}propyl]-3a,4,7,7a-tetrahydro-1H-isoindole-1,3(2H)-dione hydrochloride; m.p. 267–268° C. |
| 29. | 2-[3-{4-(2-Methoxyphenyl)piperazin-1-yl}-3-methylpropyl]-3a,4,7,7a-tetrahydro-1H-isoindole-1,3(2H)-dione hydrochloride; m.p. 219–220° C. |
| 30. | 2-[3-{4-(2-Methoxyphenyl)piperazin-1-yl}-2-methylpropyl]-3a,4,7,7a-tetrahydro-1H-isoindole-1,3(2H)-dione hydrochloride; m.p. 184–185° C. |
| 31. | 2-[3-{4-(2-Ethoxyphenyl)piperazin-1-yl}-3-methylpropyl]-3a,4,7,7a-tetrahydro-1H-isoindole-1,3(2H)-dione hydrochloride; m.p. 246–248° C. |

All the melting points reported above are uncorrected and measured by an open capillary method using Buchi 535.

PHARMACOLOGICAL TESTING RESULTS

Receptor Binding Assay

Receptor binding assays were performed using native α-adrenoceptors. The affinity of different compounds for $\alpha_{1A}$ and $\alpha_{1B}$ adrenoceptor subtypes was evaluated by studying their ability to displace specific [$^3$H]prazosin binding from the membranes of rat submaxillary and liver respectively (Michel et al, *Br J Pharmacol*, 98, 883–889 (1989)). The binding assays were performed according to U'Prichard et al. (*Eur J Pharmacol*, 50:87–89 (1978)) with minor modifications.

Submaxillary glands were isolated immediately after sacrifice. The liver was perfused with buffer (Tris HCl 50 mM, NaCl 100 mM, 10 mM EDTA pH 7.4). The tissues were homogenised in 10 volumes of buffer (Tris HCl 50 mM, NaCl 100 mM, EDTA 10 mM, pH 7.4). The homogenate was filtered through two layers of wet gauze and filtrate was centrifuged at 500 g for 10 min. The supernatant was subsequently centrifuged at 40,000 g for 45 min. The pellet thus obtained was resuspended in the same volume of assay buffer (Tris HCl 50 mM, EDTA 5 mM, pH 7.4) and were stored at −70° C. until the time of assay.

The membrane homogenates (150–250 μg protein) were incubated in 250 μl of assay buffer (Tris HCl 50 mM, EDTA 5 mM, pH 7.4) at 24–25° C. for 1 h. Non-specific binding was determined in the presence of 300 nM prazosin. The incubation was terminated by vacuum filtration over GF/B fibre filters. The filters were then washed with ice cold 50 mM Tris HCl buffer (pH 7.4). The filtermats were dried and bound radioactivity retained on filters was counted. The $IC_{50}$ & Kd were estimated by using the non-linear curve fitting program using G Pad Prism software. The value of inhibition constant Ki was calculated from competitive binding studies by using Cheng & Prusoff equation (*Cheng & Prusoff, Biochem Pharmacol*, 1973,22: 3099–3108), $Ki=IC_{50}/(1+L/Kd)$ where L is the concentration of [$^3$H] prazosin used in the particular experiment (Table I).

In Vitro Functional Studies

In order to study selectivity of action of these compounds towards different α-adrenoceptor subtypes, the ability of these compounds to antagonise $\alpha_1$-adrenoceptor agonist induced contractile response on aorta ($\alpha_{1D}$ prostate ($\alpha_{1A}$ and spleen ($\alpha_{1B}$ was studied. Aorta and spleen tissues were isolated from urethane anaesthetised (1.5 gm/kg) male wistar rats. Isolated tissues were mounted in organ bath containing Krebs Henseleit buffer of following composition (mM): NaCl 118; KCl 4.7; $CaCl_2$ 2.5; $MgSO_4 \cdot 7H_2O$ 1.2; $NaHCO_3$ 25; $KH_2PO_4$ 1.2; glucose 11.5. Buffer was maintained at 37° C. and aereated with a mixture of 95% $O_2$ and 5% $CO_2$. A resting tension of 2 g (aorta) or 1 g (spleen and prostate) was applied to tissues. Contractile response was monitored using a force displacement transducer and recorded on chart recorders. Tissues were allowed to equilibrate for 2 hours. At the end of equilibration period, concentration response curves to norepinephrine (aorta) and phenylepinephrine (spleen and prostate) were obtained in absence and presence of tested compound (at concentration of 0.1,1 and 10 mM). Antagonist affinity was calculated and expressed as $pK_B$ vales in Table II.

In Vivo Uroselectivity Study

In order to assess the uroselectivity in vivo, the effects of these compounds were studied on mean arterial pressure (MAP) and intraurethral pressure (IUP) in conscious beagle dogs as per the method of Brune et. al. (*Pharmacol* 1996, 53:356–368). Briefly, male dogs were instrumented for chronic continuous measurement of arterial blood pressure by implanting a telemetry transmitter (TL11M2-D70-PCT, Data Sci. International, St. Paul, Minn. USA) into the femoral artery, two weeks prior to the study. During the recovery period, the animal was acclimatized to stay in the sling restraint. On the day of testing, overnight fasted animal was placed in the sling restraint. A Swan-Ganz. Balloon tipped catheter was introduced into the urethra at the level of prostate and the balloon was inflated (Brune. et. al. 1996). After recording the base line readings, effect of 16 μg/kg, phenylephrine (i.v.) on MAP and IUP was recorded. The response of phenylephrine to MAP and IUP were recorded at 0.5, 1, 2, 3, 4, 6, 9 and 24 hours after the oral administration of vehicle or the test drug. The changes in MAP was recorded on line using Dataquest Software (Data Sci. International. St. Paul, Minn. USA) and IUP was recorded on a Grass Polygraph (Model 7, Grass Instruments, USA). The change in phenylephrine response on MAP and IUP administration after the test drug administration was calculated as percent change of that of control values. Area under curve was calculated and the ratio of the values for MAP and IUP was used for calculating the uroselectivity (Table III)

TABLE I

Radioligand Binding Studies
Affinity of compounds for Alpha-1 adrenoreceptor subtypes.

| Compound No. | $\alpha_{1A}$ (Rat submaxillary) Ki (nM) | $\alpha_{1B}$ (Rat liver) Ki (nM) | Selectivity $\alpha_{1B}/\alpha_{1A}$ |
|---|---|---|---|
| 01 | 0.8 | 73 | 91 |
| 02 | 83 | 398 | 4.8 |
| 03 | 32.5 | 168 | 5 |
| 04 | 80 | 363 | 4.5 |
| 05 | 259 | >500 | 2 |
| 06 | 36 | 469 | 13 |
| 07 | 183 | >500 | 2.7 |
| 08 | 0.34 | 29 | 85 |
| 09 | 0.3 | 62 | 207 |
| 10 | 62 | 165 | 2.7 |
| 11 | 0.13 | 19 | 146 |
| 12 | 8.66 | 51.3 | 5.9 |
| 13 | 6.3 | 384 | 61 |
| 14 | >500 | >500 | 1 |
| 15 | >500 | >500 | 1 |
| 16 | >500 | >500 | 1 |
| 17 | 48 | 37 | 0.78 |
| 18 | 10 | 271 | 27 |
| 19 | 5.26 | 81 | 15 |
| 20 | 46.8 | >500 | 11 |
| 21 | >500 | >500 | 1 |
| 22 | 208 | >500 | 2.4 |
| 23 | 0.16 | 28 | 175 |
| 24 | 0.24 | 28 | 117 |
| 25 | 3.3 | >500 | >151 |
| 26 | 38 | >500 | 13 |
| 27 | >500 | >500 | 1 |
| 28 | >500 | >500 | 1 |
| 29 | 3.45 | 708 | 205 |
| 30 | 48 | 611 | 13 |
| 31 | 2.1 | 232 | 110 |

TABLE II

In Vitro Functional Assays:

| Compound No. | α Adrenoceptor Subtype ($pK_B$) | | | Selectivity | |
|---|---|---|---|---|---|
| | $\alpha_{1A}$ | $\alpha_{1B}$ | $\alpha_{1D}$ | $\alpha_{1A}/\alpha_{1D}$ | $\alpha_{1A}/\alpha_{1B}$ |
| 01 | 9.27 | 7.66 | 8.64 | 4 | 41 |
| 08 | 8.93 | 8.40 | 9.05 | −1.31 | 3.4 |
| 09 | 9.17 | 7.8 | 8.6 | 3.6 | 23 |
| 11 | 9.95 | 8.28 | 8.76 | 15 | 47 |
| 13 | 8.04 | 6.09 | 7.29 | 5.6 | 89 |
| 23 | 9.94 | 7.71 | 9.91 | 1 | 170 |
| 24 | 10.4 | 7.85 | 9.27 | 13 | 355 |
| 25 | 8.90 | 7.17 | 9.00 | −1.26 | 54 |
| 29 | 7.06 | 5.8 | 7.47 | −2.57 | 18 |
| 31 | 8.3 | ND | 7.79 | 3.24 | |

TABLE III

In Vivo Uroselectivity Studies in Conscious Beagle Dogs

| Compound No. | Dose (μg/kg) | Route | Area Under Curve | | Uroselectivity Ratio |
|---|---|---|---|---|---|
| | | | MAP | IUP | IUP/MAP |
| 01 | 100 | p.o | 93 | 514 | 5.54 |
| 11 | 10 | p.o | 10 | 661 | 66 |
| 23 | 3 | p.o | 197 | 790 | 4 |
| 24 | 3 | p.o | 68 | 522 | 7.6 |

While the present invention has been described in terms of its specific embodiments, certain modifications and equivalents will be apparent to those skilled in the art and are intended to be included within the scope of the present invention.

We claim:

1. Compounds having the structure of Formula I

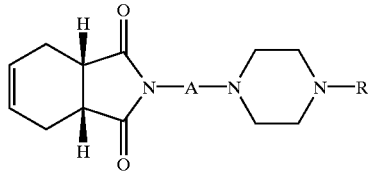

FORMULA-I and their pharmaceutically acceptable salts, enantiomers, diastereomers, N-oxides, or their polymorphs, wherein A is a straight or branched $C_1$–$C_4$ alkyl chain; R is cinnamyl, (dihalodiphenyl) methyl, monosubstituted phenyl group substituted with the substituents independently selected from the group consisting of hydroxy, nitro, or trifluoroalkoxy group, or disubstituted phenyl group substituted with the substituents independently selected from the group consisting of halogen, hydroxy, $C_1$–$C_6$ alkyl, $C_1$–$C_6$ alkoxy, trifluoromethyl, nitro, or trifluoroalkoxy group.

2. Compounds selected from the group consisting of:
2-[3-{4-(3,4-Dimethylphenyl)piperazin-1-yl}propyl]-3a,4,7,7a-tetrahydro-1H-isoindole-1,3(2H)-dione (Compound 07);
2-[3-{4-(2-Methoxy-5-fluorophenyl)piperazin-1-yl}propyl]-3a,4,7,7a-tetrahydro-1H-isoindole-1,3(2H)-dione (Compound 08);
2-[3-{4-(2,4-Difluorophenyl)piperazin-1-yl}propyl]-3a,4,7,7a-tetrahydro-1H-isoindole-1,3(2H)-dione (Compound 10);
2-[3-{4-(2-Methyl-5-chlorophenyl)piperazin-1-yl}propyl]-3a,4,7,7a-tetrahydro-1H-isoindole-1,3(2H)-dione (Compound 12);
2-[3-{4-(Cinnamyl)piperazin-1-yl}propyl]-3a,4,7,7a-tetrahydro-1H-isoindole-1,3(2H)-dione (Compound 15);
2-[3-{4-(4-Nitrophenyl)piperazin-1-yl}propyl]-3a,4,7,7a-tetrahydro-1H-isoindole-1,3(2H)-dione (Compound 16);
2-[3-{4-(3-Chloro-4-methylphenyl)piperazin-1-yl}propyl]-3a,4,7,7a-tetrahydro-1H-isoindole-1,3(2H)-dione (Compound 17);
2-[3-{4-(4-Fluoro-2-methoxyphenyl)piperazin-1-yl}propyl]-3a,4,7,7a-tetrahydro-1H-isoindole-1,3(2H)-dione (Compound 18);
2-[3-{4-(Bis-4-fluorophenyl)methylpiperazin-1-yl}propyl]-3a,4,7,7a-tetrahydro-1H-isoindole-1,3(2H)-dione (Compound 19);
2-[3-{4-(2,4-Dichlorophenyl)piperazin-1-yl}propyl]-3a,4,7,7a-tetrahydro-1H-isoindole-1,3(2H)-dione (Compound 20);
2-[3-{4-(2,4-Dimethoxyphenyl)piperazin-1-yl}propyl]-3a,4,7,7a-tetralaydro-1H-isoindole-1,3(2H)-dione (Compound 21);
2-[3-{4-(2,6-Dimethylphenyl)piperazin-1-yl}propyl]-3a,4,7,7a-tetrahydro-1H-isoindole-1,3(2H)-dione (Compound 22);
2-[3-{4-(2-Isopropoxyphenyl)piperazin-1-yl}propyl]-3a,4,7,7a-tetrahydro-1H-isoindole-1,3(2H)-dione (Compound 23);
2-[3-{4-(2-Propoxyphenyl)piperazin-1-yl}propyl]-3a,4,7,7a-tetrahydro-1H-isoindole-1,3(2H)-dione (Compound 24);
2-[3-{4-(2-n-Hexyloxyphenyl)piperazin-1-yl}propyl]-3a,4,7,7a-tetrahydro-1H-isoindole-1,3(2H)-dione (Compound 25);
2-[3-{4-(4-(2,5-Dimethoxyphenyl)piperazin-1-yl}propyl]-3a,4,7,7a-tetrahydro-1H-isoindole-1,3(2H)-dione (Compound 26);
2-[3-{4-(2-Methoxy-6-hydroxyphenyl)piperazin-1-yl}propyl]-3a,4,7,7a-tetrahydro-1H-isoindole-1,3(2H)-dione (Compound 28).

3. A method for treating benign prostatic hyperplasia in a mammal comprising administering to said mammal a compound having the structure of Formula I

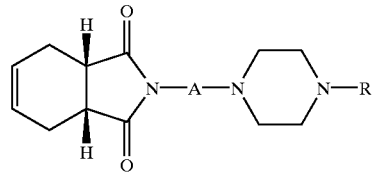

FORMULA-I or its pharmaceutically acceptable salts, enantiomers, diastereomers, N-oxides, or their polymorphs, wherein A is a straight or branched $C_1$–$C_4$ alkyl chain; R is cinnamyl, (dihalodiphenyl) methyl, benzyl, phenyl, mono- or disubstituted with the substituents independently selected from the group consisting of halogen, hydroxy, $C_1$–$C_6$ alkyl, $C_1$–$C_6$ alkoxy, trifluoromethyl, nitro, or trifluoroalkoxy group.

4. A pharmaceutical composition comprising a compound of claims 1 or 2 and a pharmaceutical acceptable carrier.

5. A method for treating benign prostatic hyperplasia in a mammal comprising administering to said mammal, the pharmaceutical composition according to claim 4.

6. A process for preparing compounds of Formula I

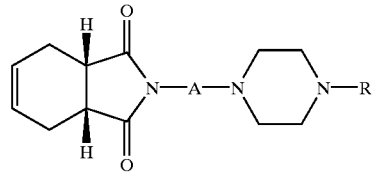

FORMULA-I and their pharmaceutically acceptable salts, enantiomers, diastereomers, N-oxides, or their polymorphs, wherein A is a straight or branched $C_1$–$C_4$ alkyl chain; R is cinnamyl, (dihalodiphenyl) methyl, monosubstituted phenyl group substituted with the substituents independently selected from the group consisting of hydroxy, nitro, or trifluoroalkoxy group, or disubstituted phenyl group substituted with the substituents independently selected from the group consisting of halogen, hydroxy, $C_1$–$C_6$ alkyl, $C_1$–$C_6$ alkoxy, trifluoromethyl, nitro, or trifloroalkoxy group, comprising reacting cis 1,2,3,6-tetrahydrophthalic anhydride of Formula II

FORMULA II

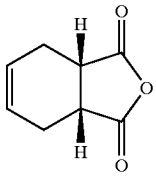

with 1-amino-4-substituted piperazinyl alkane of Formula III,

FORMULA III

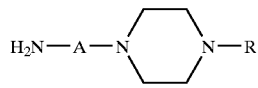

wherein A and R are as defined above, in the presence of a solvent selected from the group consisting of pyridine, n-butanol, benzene and xylene.

7. A process for preparing compounds of Formula I

FORMULA-I

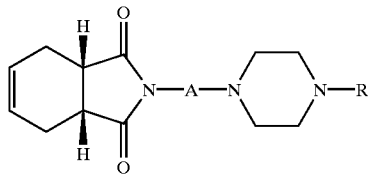

and their pharmaceutically acceptable salts, enantiomers, diastereomers, N-oxides, or their polymorphs, wherein A is a straight or branched $C_1$–$C_4$ alkyl chain; R is cinnamyl, or (dihalodiphenyl) methyl, monosubstituted phenyl group substituted with the substituents independently selected from the group consisting of hydroxyl, nitro, or trifluoroalkoxy group, or disubstituted phenyl group substituted with the substituents independently selected from the group consisting of halogen, hydroxy, $C_1$–$C_6$ alkyl, $C_1$–$C_6$ alkoxy, trifluoromethyl, nitro, or trifluoroalkoxy group, comprising reacting 1-(ω-haloalkyl)cis-3a,4,7,7a-tetrahydrophthamide of Formula IV, wherein A is as defined above,

FORMULA IV

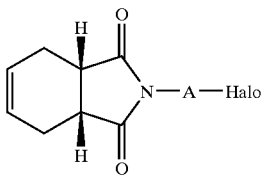

with 1-substituted piperazine of Formula V,

FORMULA V

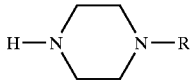

wherein R is as defined above.

* * * * *

UNITED STATES PATENT AND TRADEMARK OFFICE
CERTIFICATE OF CORRECTION

PATENT NO. : 6,914,064 B2  Page 1 of 1
APPLICATION NO. : 09/998115
DATED : July 5, 2005
INVENTOR(S) : Anand et al.

It is certified that error appears in the above-identified patent and that said Letters Patent is hereby corrected as shown below:

1. References cited, Other publications - "trifiuoromethyl" should read "trifluoromethyl"

2. References cited, Other publications - "1-piperazinyl]buty]" should read "1-piperazinyl[butyl]

3. Column 3, Line 8 - "against a 1A-adrenoceptors" should read "against 1A-adrenoceptors"

4. Column 3, Line 63 - "good a 1-adrenergic" should read "good 1-adrenergic"

5. Column 5, Compound No. 19 - "(Bis-4-fluorophenyf)" should read "(Bis-4-fluorophenyl)"

6. Column 5, Compound No. 28 - "(2-Methoxy-8-hydroxyphenyl)" should read "(2-Methoxy-6-hydroxyphenyl)"

7. Column 8, Line 34 - "piperazine-1-yl}" should read "piperazin-1-yl}"*

8. Column 8, Line 38 - "piperazine-1-yl}" should read "piperazin-1-yl}"*

9. Column 9, Compound No. 3 - "dione hydrochlolide" should read "dione hydrochloride"

10. Column 9, Compound No. 14 - "275-278 C" should read "275-276 C"

* = our error

Signed and Sealed this

Eighth Day of August, 2006

JON W. DUDAS
*Director of the United States Patent and Trademark Office*